(12) United States Patent
Nakata et al.

(10) Patent No.: US 7,741,381 B2
(45) Date of Patent: Jun. 22, 2010

(54) CURABLE COMPOSITION

(75) Inventors: Seiji Nakata, Tokyo (JP); Naoki Kakiuchi, Tokyo (JP); Hideki Kazama, Tokyo (JP)

(73) Assignees: Tokuyama Corporation, Shunan-Shi, Yamaguchi (JP); Tokuyama Dental Corporation, Taito-Ku, Tokyo (JP)

( * ) Notice: Subject to any disclaimer, the term of this patent is extended or adjusted under 35 U.S.C. 154(b) by 36 days.

(21) Appl. No.: 11/377,669

(22) Filed: Mar. 17, 2006

(65) Prior Publication Data

US 2006/0247328 A1 Nov. 2, 2006

(30) Foreign Application Priority Data

| Mar. 18, 2005 | (JP) | ............................. 2005-080128 |
| Jun. 28, 2005 | (JP) | ............................. 2005-187769 |
| Aug. 29, 2005 | (JP) | ............................. 2005-248100 |
| Dec. 28, 2005 | (JP) | ............................. 2005-377991 |

(51) Int. Cl.
*A61K 6/083* (2006.01)
*A61C 5/00* (2006.01)

(52) U.S. Cl. .................... 523/116; 524/804; 433/228.1

(58) Field of Classification Search ................ 523/116; 524/804

See application file for complete search history.

(56) References Cited

U.S. PATENT DOCUMENTS

| 3,637,563 | A | * | 1/1972 | Christena .................... 523/305 |
| 3,806,484 | A | * | 4/1974 | Stuart .......................... 524/723 |
| 4,218,294 | A |  | 8/1980 | Brack |
| 5,395,862 | A |  | 3/1995 | Neckers et al. |
| 5,500,454 | A |  | 3/1996 | Obana et al. |
| 5,639,802 | A |  | 6/1997 | Neckers et al. |
| 5,744,511 | A | * | 4/1998 | Kazama et al. ............... 522/25 |
| 5,885,837 | A |  | 3/1999 | Winkler et al. |
| 6,610,759 | B1 |  | 8/2003 | Chappelow et al. |
| 6,765,036 | B2 |  | 7/2004 | Dede et al. |
| 6,930,134 | B2 |  | 8/2005 | Suzuki et al. |
| 7,173,075 | B2 | * | 2/2007 | Wagner et al. .............. 523/116 |
| 7,449,499 | B2 | * | 11/2008 | Craig et al. ................. 523/118 |
| 2002/0071813 | A1 | * | 6/2002 | Angeletakis et al. .......... 424/49 |
| 2004/0039078 | A1 |  | 2/2004 | Suh et al. |
| 2004/0186195 | A1 |  | 9/2004 | Suzuki et al. |
| 2005/0250868 | A1 |  | 11/2005 | Suzuki et al. |
| 2006/0281663 | A1 | * | 12/2006 | Asmus ....................... 510/511 |
| 2007/0141267 | A1 | * | 6/2007 | Sonnenschein et al. .. 427/407.1 |

FOREIGN PATENT DOCUMENTS

| EP | 0127730 A2 | 12/1984 |
| EP | 0897710 A2 | 2/1999 |
| EP | 0927726 A1 | 7/1999 |
| EP | 1422254 A2 | 5/2004 |
| EP | 1431315 A2 | 6/2004 |
| JP | 07-316391 A | 12/1995 |
| JP | 11-130945 A | 5/1999 |
| JP | 2004-196949 | 7/2004 |
| WO | WO 02/13768 A2 | 2/2002 |
| WO | WO 2004/017928 A | 3/2004 |

OTHER PUBLICATIONS

XP002388935, Database WPI, Section Ch, Week 199606, Derwent Publications Ltd., London, GB, Class A18, AN 1996-056141 (corresponds to JP 07-316391).

T.Y. Lee et al., "The effect of monomer structure on oxygen inhibition of (meth)acrylates photopolymerization", Polymer, Aug. 19, 2004, pp. 6155-6162, vol, 45-No. 18, Elsevier Science Publishers B.V., GB.

\* cited by examiner

*Primary Examiner*—Tae H Yoon
(74) *Attorney, Agent, or Firm*—Buchanan Ingersoll & Rooney PC

(57) ABSTRACT

A curable composition comprising:
(A) 100 parts by mass of a monomer component which comprises a radically polymerizable monomer and has a water absorbing capacity of not larger than 20% by weight;
(B) 0.5 to 10 parts by mass of water;
(C) 0.1 to 20 parts by mass of a surfactant; and
(D) an effective amount of a radical polymerization initiator. The curable composition is cured by polymerization in a state where a water layer is formed on the surfaces of the cured body that is being formed, effectively suppressing the hindrance of polymerization caused by oxygen and decreasing the formation of unpolymerized product on the surfaces of the cured body. The curable composition is particularly useful as a dental restorative which involves difficulty when it is to be polymerized while shutting off oxygen.

4 Claims, No Drawings

CURABLE COMPOSITION

BACKGROUND OF THE INVENTION

1. Field of the Invention

The present invention relates to a curable composition for forming a cured body by radical polymerization. More specifically, the invention relates to a novel curable composition which decreases the effect of oxygen at the time of curing without an oxygen shut-off layer which is formed by applying an oxygen shut-off material.

2. Description of the Related Art

A curable composition contains a polymerizable monomer and a polymerization initiator as basic components. When the curable composition forms a cured body by radical polymerization, an unpolymerized layer forms on the surfaces of the cured body that are exposed to the air if the step of polymerization is conducted in the air. This is because on the surfaces of the curable composition exposed to the air, oxygen in the air turns into peroxide radicals upon being bonded to the radical of the polymerizable monomer, and the polymerization no longer proceeds.

To provide a cured body without unpolymerized layer on the surfaces, it was so far attempted to radically polymerize the curable composition while shutting off the contact with the air by effecting the curing in the nitrogen atmosphere or in the water or by using an oxygen shut-off material (see, for example, patent documents 1 and 2).

Patent document 1: JP-A-2000-128723
Patent document 2: JP-A-2004-284969

A method of curing a (meth)acrylic polymerizable monomer by radical polymerization has been widely utilized in the dental field. This method has been applied to dental cements, dental adhesives (bonding materials), composite resins, resins for imparting luster to the surfaces of the resin tooth material, and tooth manicure. When the dentally restored material has an unpolymerized layer on the surfaces of the cured body, the surface hardness and color are deteriorated. Besides, the unpolymerized layer present on the surfaces gets entangled with the polishing bur at the time of polishing and grinding the cured body, and hinders the polishing work.

In the dental therapy, the above dental restorative is in many cases directly cured in the oral cavity. If there is employed a method of decreasing the formation of unpolymerized product by effecting the curing in the water or in the nitrogen atmosphere, the curable composition must be once taken out from the oral cavity causing, however, the shape formed in the oral cavity to be deformed. Formation of the oxygen shut-off layer involves difficulty in many cases and, besides, the oxygen shut-off material cannot be used for the materials having low viscosities, such as bonding materials.

Thus, the methods described in the patent documents 1 and 2 are not suited for the dental restoratives, and it has been desired to provide a technology for decreasing the effect of oxygen at the time of curing without providing oxygen shut-off layer.

On the other hand, when a radically polymerizable monomer to which a surfactant is added is used as an adhesive to a hard tissue such as teeth, there has been reported that the curable composition that is obtained stimulates the dental pulp less and permeates less into the dentin (see patent document 3).

Patent document: JP-A-7-316391

The patent document 3 further discloses adding water as a diluting solvent. However, the diluting solvent is used when a surfactant component is used as a primer. For example, the primer (often includes a radically polymerizable monomer) containing water and a surfactant is applied to the teeth and dried. Thereafter, a component containing the radically polymerizable monomer and a polymerization initiator is applied to effect the curing by polymerization. In the patent document 3, therefore, no water is existing at the time of curing, and the water does not affect the formation of the unpolymerized product.

SUMMARY OF THE INVENTION

It is an object of the present invention to provide a curable composition which effectively suppresses the formation of the unpolymerized layer on the surfaces without the need of using oxygen shut-off material when the curing is effected by radical polymerization in an environment where oxygen is present.

Another object of the present invention is to provide a curable composition that can be effectively used as a dental restorative.

To achieve the above objects, the present inventors have conducted keen study. As a result, the inventors have discovered the fact that use of a particular radically polymerizable monomer in combination with small amounts of water and a surfactant makes it possible to effectively lower the hindering of polymerization caused by oxygen, and have finished the present invention based on the above novel discovery.

According to the present invention, there is provided a curable composition comprising:

(A) 100 parts by mass of a monomer component which comprises a radically polymerizable monomer and has a water absorbing capacity of not larger than 20% by weight;
(B) 0.5 to 10 parts by mass of water;
(C) 0.1 to 20 parts by mass of a surfactant; and
(D) an effective amount of a radical polymerization initiator.

In the curable composition of the present invention, it is desired that:

(1) the monomer component (A) is a mixture of a strongly hydrophobic polymerizable monomer (a-1) having a water absorbing capacity of not larger than 5% by weight and a strongly hydrophilic polymerizable monomer (a-2) having a water absorbing capacity of not smaller than 100% by weight;
(2) the surfactant (C) comprises an anionic surfactant (c-1) and a nonionic surfactant (c-2);
(3) the anionic surfactant (c-1) is contained in an amount of 0.1 to 10 parts by mass and the nonionic surfactant (c-2) is contained in an amount of 0.1 to 10 parts by mass per 100 parts by mass of the monomer component (A); and
(4) a water-soluble polymer (E) is contained in an amount of 0.00001 to 10 parts by mass per 100 parts by mass of the monomer component (A).

In the present invention, the water absorbing capacity of the monomer component is calculated according to the Karl Fischer's method from the water content in the monomer component which is the radically polymerizable monomer that has absorbed water to its saturation at 23° C., and is given by the following formula, Water absorbing capacity=[water content $(g)$/weight $(g)$ of monomer Component $(A)$]×100

The curable composition of the present invention containing the above components (A) to (D) and, as required, the component (E) gives a cured product effectively suppressing the formation of the unpolymerized layer on the surfaces that come in contact with oxygen without the need of using any particular means such as oxygen shut-off material even when the curing is conducted by polymerization in an environment where oxygen is present. Since formation of the unpolymerized layer is suppressed, the cured body exhibits excellent properties such as mechanical strength and durability. For example, even when a cured body is formed by radical polymerization in a state where at least part of the surface of the curable composition is exposed to the atmosphere containing oxygen, formation of the unpolymerized layer is effectively suppressed on the surfaces of the cured body. Therefore, the cured body that is obtained exhibits excellent properties required by a dental restorative, such as polishing property. The above curable composition is very useful particularly as a dental restorative.

DETAILED DESCRIPTION OF THE INVENTION

The curable composition of the present invention contains a monomer component (A) which comprises a radically polymerizable monomer and a polymerization initiator (D). Here, a particularly important feature resides in the selective use of a particular radically polymerizable monomer such that the water absorbing capacity of the monomer component (A) becomes not larger than a predetermined value (not larger than 20% by weight) and in the use of the water (component B) and the surfactant (component C) in combination with the monomer component (A) of which the water absorbing capacity is thus adjusted.

That is, in the above curable composition, the monomer component (A) which is the radically polymerizable monomer is polymerized by the action of the polymerization initiator to give a cured body. In this case, since the polymerization undergoes in the presence of the water and the surfactant, the layer of the surfactant and water is formed on the surfaces of the cured body at the time when the radically polymerizable monomer is cured; i.e., the layer of the surfactant and water hinders oxygen from infiltrating into the cured body and, as a result, unpolymerized product is formed in decreased amounts on the surfaces of the cured body. Here, however, the water and the surfactant must be present maintaining a predetermined balance on the surfaces of the cured body formed accompanying the polymerization. When, for example, the water or the surfactant is present in very large amounts, the strength of the cured body decreases or the curing does not at all take place depending upon the cases. In the present invention, therefore, the water absorbing capacity of the monomer component (A) must be adjusted to lie within a predetermined range and, besides, the amounts of the water (component B) and the surfactant (C) per the monomer component (A) must be adjusted to lie within predetermined ranges. These components will now be described in detail.

<Monomer Components (A)>

In the present invention, a radically polymerizable monomer is used as the monomer component (A). Here, however, the monomer component (A) must have the water absorbing capacity which is not larger than 20% by weight as measured by the above-mentioned method. As the monomer component (A), therefore, there is used a single kind of the radically polymerizable monomer having a water absorbing capacity of not larger than 20% by weight. Or, as the monomer component (A), there is used a mixture of a radically polymerizable monomer having a water absorbing capacity of not larger than 20% by weight and a radically polymerizable monomer having a water absorbing capacity of larger than 20% by weight, of which the amounts are so adjusted that the water absorbing capacity is not larger than 20% by weight. Therefore, even a hydrophilic radically polymerizable monomer which by itself has a high water absorbing capacity (water absorbing capacity of not smaller than 100% by weight) such as a hydroxyethyl methacrylate can be used as the monomer component (A) in the form of a mixture having a water absorbing capacity of not larger than 20% by weight in combination with a hydrophobic radically polymerizable monomer having a small water absorbing capacity.

That is, in the present invention, when the monomer component (A) has a water absorbing capacity which is not smaller than 20% by weight, it is considered that the layer of water is not formed on the surfaces of the cured body that is formed accompanying the progress of curing by polymerization and, hence, formation of the unpolymerized product on the surfaces of the cured body cannot be decreased.

In the curable composition of the present invention, to obtain a cured body having more excellent mechanical properties by enhancing the effect for suppressing the formation of unpolymerized product on the surfaces of the cured body, it is desired that the monomer component (A) has a water absorbing capacity in a range of 0.1 to 15% by weight and, most desirably, 0.5 to 5% by weight.

So far as the water absorbing capacity is adjusted to lie within the above-mentioned range as described above, there can be used a variety of radically polymerizable monomers as the monomer component (A). In particular, a (meth)acrylic polymerizable monomer can be desirably used from the standpoint of excellent polymerization property and curability near room temperature. There can be used a single kind of, or a combination of two or more kinds of, the (meth)acrylic polymerizable monomers depending upon their water absorbing capacities in such a manner that the water absorbing capacity of the monomer component (A) lies within the above-mentioned range.

As described above, the water absorbing capacity of the monomer component (A) can be found relying upon the Karl Fischer's method. However, whether the water absorbing capacity is not larger than 20% by weight can be simply judged by mixing 100 parts by mass of the polymerizable monomer and 20 parts by mass of the water to see if the mixture is becoming homogeneous. That is, it can be so judged that the water absorbing capacity is not smaller than 20% by weight when the mixture is homogeneous and that the water absorbing capacity is not larger than 20% by weight when the mixture is not homogeneous.

As the hydrophobic (meth)acrylic polymerizable monomer having by itself a water absorbing capacity of not larger than 20% by weight, there can be exemplified the following compounds. Values in parenthesis represent water absorbing capacities. Besides, the water absorbing capacity added (*) is an assumed value range from the molecule structure.

Polyethoxylation trimethylolpropane having six oxyethylene groups in average (*5 to 10 wt %),
Ethoxylation bisphenol A dimethacrylate trimethacrylate having ten oxyethylene groups in average (*5 to 10 wt %),
Polyethoxylation bisphenol A dimethacrylate having thirteen oxyethylene groups in average (*10 to 20 wt %),
Polyethoxylation trimethylolpropane having nine oxyethylene groups in average (*10 to 20 wt %),
Hydroxypentyl methacrylate (*10 to 20 wt %),
Hydroxybutyl methacrylate (*10 to 20 wt %),
Glycerol dimethacrylate (*10 to 20 wt %),
Methyl methacrylate (1.5 wt %),
Ethyl methacrylate (not larger than 1.0 wt %),
Butyl methacrylate (not larger than 1.0 wt %),
Isopropyl methacrylate (not larger than 1.0 wt %), Acetoacetoxyethyl methacrylate (1.8 wt %),
2,2-Bis(methacryloyloxyphenyl)propane (not larger than 1.0 wt %),
2,2-Bis[4-(3-methacryloyloxy)-2-hydroxypropoxyphenyl]propane (2.2 wt %),
2,2-Bis(4-methacryloyloxyphenyl)propane (not larger than 0.5 wt %),
2,2-Bis(4-methacryloyloxypolyethoxyphenyl)propane (0.5 wt %),
2,2-Bis(4-methacryloyloxydiethoxyphenyl)propane (not larger than 1.0 wt %),
2,2-Bis(4-methacryloyloxytetraethoxyphenyl)propane (*1 to 5 wt %),
2,2-Bis(4-methacryloyloxypentaethoxyphenyl)propane (*1 to 5 wt %),
2,2-Bis(4-methacryloyloxydipropoxyphenyl)propane (*1 to 5 wt %),
2(4-Methacryloyloxydiethoxyphenyl)-2(4-methacryloyloxydiethoxyphenyl)propane (*1 to 5 wt %),
2(4-Methacryloyloxydiethoxyphenyl)-2(4-methacryloyloxy di-triethoxyphenyl)propane (*1 to 5 wt %),
2(4-Methacryloyloxydipropoxyphenyl)-2(4-methacryloyloxytriethoxyphenyl)propane (*1 to 5 wt %),
2,2-Bis(4-methacryloyloxypropoxyphenyl)propane (*1 to 5 wt %),
2,2-Bis(4-methacryloyloxyisopropoxyphenyl)propane (*1 to 5 wt %),
Monoethylene glycol dimethacrylate (not larger than 1.0 wt %),
Diethylene glycol dimethacrylate (*1 to 5 wt %),
Triethylene glycol dimethacrylate (1.7 wt %),
Tetraethylene glycol dimethacrylate (*1 to 5 wt %),
1,3-Butanediol dimethacrylate (not larger than 0.5 wt %),
1,4-Butanediol dimethacrylate (not larger than 0.5 wt %),
1,6-Hexanediol dimethacrylate (0.1 wt %),
Nonamethylenediol methacrylate (0.1 wt %),
Trimethylolpropane trimethacrylate (*1 to 5 wt %),
Trimethylolethane trimethacrylate (*1 to 5 wt %),
Pentaerythritol trimethacrylate (*1 to 5 wt %),
Trimethylolmethane trimethacrylate (*1 to 5 wt %), and
Pentaerythritol tetramethacrylate (*1 to 5 wt %)

Among the above compounds, the present invention uses, particularly, a strongly hydrophobic (meth)acrylic polymerizable monomer (a-1) having a water absorption capacity of not larger than 5% by weight, i.e., preferably uses the compounds described below.

Strongly Hydrophobic (Meth)Acrylic Polymerizable Monomers (a-1):
2,2-Bis(methacryloyloxyphenyl)propane (0.5 wt %),
2,2-Bis[4-(3-methacryloyloxy)-2-hydroxypropoxyphenyl]propane (2.2 wt %),
2,2-Bis(4-methacryloyloxyphenyl)propane (not larger than 1.0 wt %),
2,2-Bis(4-methacryloyloxypolyethoxyphenyl)propane (0.5 wt %),
2,2-Bis(4-methacryloyloxydiethoxyphenyl)propane (not larger than 1.0 wt %),
2,2-Bis(4-methacryloyloxytetraethoxyphenyl)propane (*1 to 5 wt %),
2,2-Bis(4-methacryloyloxypentaethoxyphenyl)propane (*1 to 5 wt %),
2,2-Bis(4-methacryloyloxydipropoxyphenyl)propane (*1 to 5 wt %),
2(4-Methacryloyloxydiethoxyphenyl)-2(4-methacryloyloxydiethoxyphenyl)propane (*1 to 5 wt %),
2(4-Methacryloyloxydiethoxyphenyl)-2(4-methacryloyloxydi-triethoxyphenyl)propane (*1 to 5 wt %),
2(4-Methacryloyloxydipropoxyphenyl)-2(4-methacryloyloxytriethoxyphenyl)propane (*1 to 5 wt %),
2,2-Bis(4-methacryloyloxypropoxyphenyl)propane (*1 to 5 wt %),
2,2-Bis(4-methacryloyloxyisopropoxyphenyl)propane (*1 to 5 wt %),
1,3-Butanediol dimethacrylate (not larger than 0.5 wt %),
1,4-Butanediol dimethacrylate (not larger than 0.5 wt %),
1,6-Hexanediol dimethacrylate (0.1 wt %),
Nonamethylenediol dimethacrylate (0.1 wt %),
Monoethylene glycol dimethacrylate (not larger than 0.5 wt %),
Diethylene glycol dimethacrylate (*1 to 5 wt %),
Triethylene glycol dimethacrylate (1.7 wt %) and
Tetraethylene glycol dimethacrylate (*1 to 5 wt %)

There are many (meth)acrylic polymerizable monomers having water absorbing capacities which are not larger than 20% by weight. In the present invention, however, it is particularly desired to select strongly hydrophilic (meth)acrylic polymerizable monomer (a-2) having a water absorbing capacity of not smaller than 100% by weight and to use it in combination with the above-mentioned hydrophobic (meth)acrylic polymerizable monomer having a water absorbing capacity of not larger than 20% by weight and, particularly, a strongly hydrophobic (meth)acrylic polymerizable monomer (a-1) having a water absorbing capacity of not larger than 5% by weight as a mixture having a water absorbing capacity of not larger than 20% by weight (desirably, 0.1 to 15% by weight and, most desirably, 0.5 to 5% by weight). An embodiment of using the hydrophobic radically polymerizable monomer in combination with the hydrophilic radically polymerizable monomer is highly effective in suppressing the formation of unpolymerized product on the surfaces of the cured body. In particular, a combination of the strongly hydrophobic (meth)acrylic polymerizable monomer and the strongly hydrophilic (meth)acrylic polymerizable monomer makes it possible to greatly decrease the formation of the unpolymerized product as demonstrated in Examples appearing later. As the strongly hydrophilic (meth)acrylic polymerizable monomer (a-2) having a water absorbing capacity of not smaller than 100% by weight, there can be exemplified the following compounds. All of the following compounds are strongly hydrophilic and can be dissolved in water without limit, and the water absorbing capacity of those compounds exceed to 100% by weight.

Strongly Hydrophilic (Meth)Acrylic Polymerizable Monomers (a-2):
Acrylic acid,
Methacrylic acid,
2-Hydroxyethyl(meth)acrylate,
2-Hydroxypropyl(meth)acrylate,
3-hydroxypropyl(meth)acrylate,
1,3-Dihydroxypropyl(meth)acrylate,
2,3-Dihydroxypropyl(meth)acrylate,
(Meth)acrylamide,
2-Hydroxyethyl(meth)acrylamide,
Dimethacrylate of polyethylene glycol having an average molecular weight of not smaller than 400,
Methacrylate of polyethylene glycol having an average molecular weight of not smaller than 400,
2-Methacryloyloxyethyldihydrogen phosphate, and
ethoxylation bisphenol A dimethacrylate having 25 or more oxyethylene groups in average Though the reason is not yet clear why use of the hydrophobic radically polymerizable monomer in combination with the hydrophilic radically polymerizable monomer enhances the effect of lowering the formation of unpolymerized product on the surfaces as in the present invention, it is presumed that the hydrophilic radically polymerizable monomer that is contained enhances the dispersion of water to the curable composition contributing to improving homogeneity of the layer of the surfactant and the water formed on the surfaces when the curable composition is being cured.

When a mixture of two or more kinds of radically polymerizable monomers is used as the monomer component (A) as described above, the water absorbing capacity of the mixture can be roughly calculated as an arithmetic mean from the water absorbing capacities of the individual radically polymerizable monomers. Therefore, the mixing ratio may be adjusted based roughly on the arithmetic mean such that the water absorbing capacity of the monomer component (A) lies within the above-mentioned range. For example, when a mixture of the strongly hydrophobic radically polymerizable monomer and the strongly hydrophilic radically polymerizable monomer is to be used as the monomer component (A), the strongly hydrophobic radically polymerizable monomer may be used in large amounts to adjust the water absorbing capacity to lie within the above-mentioned range.

In the present invention, further, a variety of kinds of radically polymerizable monomers can be used in a single kind or in a combination of two or more kinds so far as the water absorbing capacity of the monomer component (A) (water absorbing capacity of the radically polymerizable monomers as a whole) is adjusted to lie within the above-mentioned range. By using a bifunctional, a trifunctional or a more highly functional monomer in a large amount, the finally obtained cured body exhibits improved mechanical properties such as the strength, durability and the like properties.

In addition to the above (meth)acrylic polymerizable monomer, further, the curable composition of the present invention may be further blended with radically polymerizable monomers other than the above (meth)acrylic polymerizable monomer for easy polymerization and for adjusting the viscosity and other properties. In this case, too, the radically polymerizable monomer component must have a water absorbing capacity of not larger than 20% by weight, as a matter of course. Examples of the other radically polymerizable monomers include fumaric esters, such as monomethyl fumarate, diethyl fumarate and diphenyl fumarate; styrenes or α-methylstyrene derivatives, such as styrene, divinylbenzene and α-methylstyrene; and allyl compounds, such as diallyl terephthalate, diallyl phthalate and diallyl diglycol carbonate. These other radically polymerizable monomers may also be used in a single kind or in a combination of two or more kinds.

<Water (Component B)>

In the curable composition of the present invention, water is dispersed in a matrix of the above-mentioned monomer component (A), and the curing is conducted by radical polymerization in a state where the water is dispersed to form the cured body. That is, the radical polymerization is conducted in a state where the water is dispersed together with the surfactant that will be described later. Therefore, a water layer (containing the surfactant) is formed to a suitable degree on the surfaces of the cured body accompanying the progress of polymerization, the water layer suppressing oxygen from infiltrating into the cured body and, as a result, suppressing the formation of unpolymerized product on the surfaces of the cured body.

Water is blended in an amount of 0.5 to 10 parts by mass, preferably, 0.5 to 5 parts by mass and, most preferably, 1 to 3 parts by mass per 100 parts by mass of the monomer component (A). That is, formation of the unpolymerized product decreases with an increase in the amount of blending water resulting, however, in a decrease in the mechanical properties such as strength and hardness of the cured body. When the curing is conducted by polymerization in water instead of being blended with water, there exists no problem from the standpoint of lowering the formation of the unpolymerized product causing, however, the mechanical properties of the cured body to be greatly impaired or the curing to become insufficient and, besides, making it necessary to immerse the curable composition in water, imposing great limitation on the use of the curable composition and making it difficult to use the curable composition for such applications as dental restoratives. According to the present invention, the water is dispersed in the above-mentioned amount in the curable composition.

<Surfactants (Component C)>

The curable composition of the present invention is blended with the surfactant together with the water. That is, use of the surfactant makes it possible to distribute the water layer on the surfaces of the cured body that is formed accompanying the progress of polymerization and to effectively decrease the formation of the unpolymerized product on the surfaces of the cured body.

The surfactant is used in an amount of 0.1 to 20 parts by mass per 100 parts by mass of the monomer component (A). Like in the case of blended with water, formation of the unpolymerized product on the surfaces decreases with an increase in the amount of blending the surfactant resulting, however, in a decrease in the mechanical properties of the cured body. Therefore, the amount of blending the surfactant is limited to lie within the above-mentioned range.

As the surfactant, there can be used either an ionic surfactant such as anionic, cationic or amphoteric ionic surfactant, or a nonionic surfactant. Though not limited thereto only, concrete examples of the surfactant are as described below.

Anionic Surfactants:
  Alkyl sulfates such as sodium decyl sulfate and sodium lauryl sulfate;
  Alkyl sulfonates such as sodium hexane sulfonate and sodium decyl sulfonate;
  Alkylbenzene sulfonates such as sodium decylbenzene sulfonate and sodium laurylbenzene sulfonate;
  Metal salt of aliphatic carboxylates such as sodium laurate, sodium stearate and sodium oleate;
  Metal salts of higher alkylether sulfuric esters, such as sodium laurylether sulfuric ester obtained by sulfating an adduct of a lauryl alcohol and an ethylene oxide;
  Sulfosuccinic diesters such as sodium sulfosuccinate;
  Phosphoric esters of higher alcohol ethylene oxide adducts;

Cationic Surfactants:
  Alkylamine salts such as dodecylammonium chloride;
  Quaternary ammonium salts such as trimethyldodecylammonium bromide.

Amphoteric Ionic Surfactants:
  Alkyldimethylamine oxides such as dodecyldimethylamine oxide;
  Alkylcarboxybetaines such as dodecylcarboxybetaine;
  Alkylsulfobetaines such as dodecylsulfobetaine;
  Salts of amide amino acid, such as lauramidepropylamine oxide;

Nonionic Surfactants:
  Polyoxyethylenealkyl ethers such as polyoxyethylenelauryl ether;
  Polyoxyethylenealkylphenyl ethers such as polyoxyethylenelaurylphenyl ether;
  Fatty acid polyoxyethylene esters such as fatty acid polyoxyethylenelauryl ester;
  Polyoxyethylenesorbitan esters such as polyoxyethylenesorbitanlauryl ester;

In the present invention, the above-mentioned surfactants can be used in one kind or in a combination of two or more kinds. Particularly desirably, however, the anionic surfactant (c-1) and the nonionic surfactant (c-2) are used in combination. That is, as will become obvious from Examples appearing later, when the two kinds of surfactants are used in combination, the effect is greatly improved for suppressing the formation of unpolymerized product on the surfaces of the cured body at the time of hardening by polymerization as compared to when a single surfactant is used.

Further, the curable composition blended with the anionic surfactant involves a problem of low preservation stability at low temperatures. That is, a curable composition blended with a radically polymerizable monomer and a polymerization initiator often undergoes the curing by polymerization while being preserved. Therefore, the curable composition is often cold-preserved (e.g., 0 to 10° C.) and is cured by polymerization upon being returned back to room temperature when it is to be used. In such a case, the anionic surfactant that is blended precipitates decreasing the effect for suppressing the formation of the unpolymerized product. However, when the anionic surfactant (c-1) and the nonionic surfactant (c-2) are used in combination, the anionic surfactant can be effectively prevented from being precipitated when cold-preserved, and the curable composition can be preserved maintaining enhanced stability.

When the anionic surfactant (c-1) and the nonionic surfactant (c-2) are used in combination, the anionic surfactant (c-1) that is used is the one having an HLB (hydrophilic-lipophilic balance) of 20 to 50 and, particularly, 30 to 50 among the compounds exemplified above from the standpoint of suppressing the formation of unpolymerized product on the surfaces and is, most preferably, an alkyl sulfate, an alkyl sulfonate or an alkylbenzene sulfonate (among them, the one in which a carbon chain of the alkyl group has 6 to 16 carbon atoms). As the nonionic surfactant (c-2), there is preferably used the one having an HLB of not smaller than 3 and, particularly, 6 to 18 among the compounds exemplified above. When these surfactants are to be used in combination, further, it is desired to use the anionic surfactant (c-1) in an amount of 0.1 to 10 parts by mass and, particularly, in an amount of 0.3 to 3 parts by mass, and to use the nonionic surfactant (c-2) in an amount of 0.1 to 10 parts by mass and, particularly, 0.3 to 3 parts by mass per 100 parts by mass of the monomer component (A) from the standpoint of suppressing the formation of the unpolymerized product and preservation stability.

<Polymerization Initiators (Component D)>

The curable composition of the present invention is blended with a polymerization initiator for polymerizing the monomer component (A). Any widely known polymerization initiator can be used without limitation provided it is capable of polymerizing and curing the radically polymerizable monomer that is used as the monomer component (A). As the polymerization initiators used in the dental field, there are used, for example, a chemical polymerization initiator (normal temperature redox initiator), a photopolymerization initiator and a heat polymerization initiator. Considering the curing in the oral cavity, however, it is desired to use the chemical polymerization initiator and/or the photopolymerization initiator. Described below are a variety of polymerization initiators.

-Chemical Polymerization Initiators-

The chemical polymerization initiator is the one containing two or more components and produces polymerization activating species near room temperature when the whole components are mixed together just before the use. The chemical polymerization initiator can be represented by those of the amine compounds/organic peroxides.

As the amine compound used as the chemical polymerization initiator, there can be exemplified an aromatic amine such as N,N-dimethyl-p-toluidine, N,N-dimethylaniline and N,N-diethanol-p-toluidine.

Further, representative examples of the organic peroxide used as the chemical polymerization initiator include ketone peroxide, peroxyketal, hydroperoxide, diaryl peroxide, peroxy ester, diacyl peroxide and peroxydicarbonate. Concrete examples are as described below.

Ketone Peroxides:
  Methyl ethyl ketone peroxide, cyclohexanone peroxide, methylcyclohexanone peroxide, methylacetoacetate peroxide and acetylacetone peroxide Peroxyketals:
1,1-Bis(t-hexylperoxy)-3,3,5-trimethylcyclohexane,
1,1-Bis(t-hexylperoxy)cyclohexane,
1,1-Bis(t-butylperoxy)-3,3,5-trimethylcyclohexanone,
1,1-Bis(t-butylperoxy)cyclohexane,
1,1-Bis(t-butylperoxy)cyclodecane,
2-2-Bis(t-butylperoxy)butane,
N-butyl 4,4-bis(t-butylperoxy)valerate, and
2,2-Bis(4,4-di-t-butylperoxycyclohexyl)propane Hydroperoxides:
p-methane hydroperoxide,
Diisopropylbenzene peroxide,
1,1,3,3-Tetramethylbutyl hydroperoxide,
Cumene hydroperoxide,
t-Hexyl hydroperoxide, and
t-Butyl hydroperoxide Dialkyl Peroxides:
α,α-Bis(t-butylperoxy)diisopropylbenzene,
Dicumyl peroxide,
2,5-Dimethyl-2,5-bis(t-butylperoxy)hexane,
t-Butylcumyl peroxide,
Di-t-butyl peroxide, and
2,5-Dimethyl-2,5-bis(t-butylperoxy)hexane-3

Diacyl Peroxides:
Isobutyl peroxide,
2,4-Dichlorobenzoyl peroxide,
3,5,5-Trimethylhexanoyl peroxide,
Octanoyl peroxide,
Lauroyl peroxide,
Stearyl peroxide,
Succinic acid peroxide,
m-Toluoylbenzoyl peroxide, and
Benzoyl peroxide Peroxycarbonates:
Di-n-propylperoxy dicarbonate,
Diisopropylperoxy dicarbonate,
Bis(4-t-butylcyclohexyl)peroxy dicarbonate,
Di-2-ethoxyethylperoxy dicarbonate, Di-2-ethylhexylperoxy dicarbonate,
Di-2-methoxybutylperoxy dicarbonate, and
  Di(3-methyl-3-methoxybutyl)peroxy dicarbonate Peroxyesters:
α,α-Bis(neodecanoylperoxy)diisopropylbenzene,
Cumylperoxyneodecanoate,
1,1,3,3-Tetramethylbutylperoxyneodecanoate,
1-Cyclohexyl-1-methyl ethyl peroxyneodecanoate,
t-Hexylperoxyneodecanoate,
t-Butylperoxyneodecanoate,
t-Hexylperoxy pivarate,
t-Butylperoxy pivarate,
1,1,3,3-Tetramethylbutylperoxy-2-ethylhexanoate,
2,5-Dimethyl-2,5-bis(2-ethylhexanoylperoxy)hexane,
1-Cyclohexyl-1-methyl ethyl peroxy-2-ethylhexanoate,
t-Hexylperoxy-2-ethylhexanoate,
t-Butylperoxy-2-ethylhexanoate,
t-Butylperoxyisobutylate,
t-Hexylperoxyisopropylmonocarbonate,
t-Butylperoxymaleic acid,
t-Butylperoxy-3,5,5-trimethylhexanoate,
t-Butylperoxylaurate,
2,5-Dimethyl-2,5-bis(m-toluoylperoxy)hexane,
t-Butylperoxyisopropyl monocarbonate,
t-Butylperoxy-2-ethylhexyl monocarbonate,
t-Hexylperoxybenzoate,
2,5-Dimethyl-2,5-bis(benzoylperoxy)hexane,
t-Butylperoxyacetate,
t-Butylperoxy-m-toluoylbenzoate,
t-Butylperoxybenzoate, and
Bis(t-butylperoxy)isophthalate Other Organic Peroxides:
t-Butyltrimethylsilyl peroxide, and
3,3',4,4'-Tetra(t-butylperoxycarbonyl)benzophenone The organic peroxides may be suitably selected and may be used in one kind or in two or more kinds in combination. Among them, a hydroperoxide, a ketone peroxide, a peroxy ester and a diacyl peroxide can be particularly preferably used from the standpoint of polymerization activity. Among them, further, it is desired to use an organic peroxide having a 10-hour half-value period temperature of not lower than 60° C. from the standpoint of preservation stability when a curable composition is prepared.

There is no problem even when the chemical polymerization initiator comprising the organic peroxide and the amine compound is further blended with a sulfinic acid such as benzenesulfinic acid, p-toluenesulfinic acid or a salt thereof, or a barbituric acid initiator such as 5-butylbarbituric acid.

It is further allowable to use a chemical polymerization initiator of the type of aryl borate compound/acidic compound which utilizes the production of radicals by decomposing the aryl borate compound with an acid.

The aryl borate compound may be any known compound without particular limitation provided it has at least one boron-aryl bond in a molecule thereof. It is, however, desired to use an aryl borate compound having three or four boron-aryl bonds in one molecule from the standpoint of preservation stability. From the standpoint of easy handling, synthesis or availability, further, it is desired to use an aryl borate compound having four boron-aryl bonds. There can be exemplified the following aryl borate compounds.

Borate Compounds Having Three Boron-Aryl Bonds in a Molecule:
As the aryl borate compound, there can be exemplified sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts and butylquinolinium salts of the following boron compounds:
Monoalkyltriphenylboron,
Monoalkyltris(p-chlorophenyl)boron,
Monoalkyltris(p-fluorophenyl)boron,
Monoalkyltris(3,5-bistrifluoromethyl)phenylboron,
Monoalkyltris[3,5-bis(1,1,1,3,3,3-hexafluoro-2-methoxy-2-propyl)phenyl]boron,
Monoalkyltris(p-nitrophenyl)boron,
Monoalkyltris(m-nitrophenyl)boron,
Monoalkyltris(p-butylphenyl)boron,
Monoalkyltris(m-butylphenyl)boron,
Monoalkyltris(p-butyloxyphenyl)boron,
Monoalkyltris(m-butyloxyphenyl)boron,
Monoalkyltris(p-octyloxyphenyl)boron, and
Monoalkyltris(m-octyloxyphenyl)boron (in all of these compounds, however, alkyl represents any one of n-butyl, n-octyl or n-dodecyl).

Borate Compounds Having Four Boron-Aryl Bonds in a Molecule:
As the aryl borate compound, there can be exemplified sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts and butylquinolinium salts of the following boron compounds:
Tetraphenylboron,
Tetrakis(p-chlorophenyl)boron,
Tetrakis(p-fluorophenyl)boron,
Tetrakis(3,5-bistrifluoromethyl)phenylboron,
Tetrakis[3,5-bis(1,1,1,3,3,3-hexafluoro-2-methoxy-2-propyl)phenyl]boron,
Tetrakis(p-nitrophenyl)boron,
Tetrakis(m-nitrophenyl)boron,
Tetrakis(p-butylphenyl)boron,
Tetrakis(m-butylphenyl)boron,
Tetrakis(p-butyloxyphenyl)boron,
Tetrakis(m-butyloxyphenyl)boron,
Tetrakis(p-octyloxyphenyl)boron, and
Tetrakis(m-octyloxyphenyl)boron (in all of these compounds, however, alkyl represents any one of n-butyl, n-octyl or n-dodecyl).

Each kind of aryl borate compounds exemplified above may be used in combination with two or more.

As the acidic compound to be used in combination with the aryl borate compound, there can be preferably used an acidic group-containing radically polymerizable monomer. The radically polymerizable monomer to be used as the acidic compound may be the one that has at least one radically polymerizable unsaturated group and at least one acidic group, respectively, in a molecule. The acidic group so acts that the aqueous solution or the water suspension of the radically polymerizable monomer exhibits acidity, and may be a carboxyl group (—COOH), a sulfo group (—SO$_3$H), a phosphinico group {=P(=O)OH} or a phosphono group {—P(=O)(OH)$_2$}. Further, the above acidic group may be present in a molecule in the form of an acid anhydride structure in which two acidic groups are dehydrated and condensed or may be present in the molecule as an acid halide group in which a hydroxyl group of an acidic group is substituted with a halogen.

As the acidic group-containing radically polymerizable monomer, there can be preferably used a radically polymerizable monomer of the type of (meth)acrylic acid exemplified above concerning the monomer components (A).

When the acidic group-containing radically polymerizable monomer is to be used as the polymerization initiator in combination with the aryl borate compound, the water absorbing capacity of the monomer component (A) must be adjusted to lie within the above-mentioned range while incorporating the acidic group-containing radically polymerizable monomer therein since the acidic group-containing radically polymerizable monomer is contained in the monomer component (A).

The above-mentioned polymerization initiator of the type of aryl borate compound/acidic compound may further be used in combination with an organic peroxide and/or a transition metal compound. The organic peroxides are as described above. As the transition metal compounds, further, there can be used a vanadium compound having a valency of +IV or +V. Concrete examples of the vanadium compound include divanadium tetraoxide (IV), vanadium oxide acetylacetonato (IV), vanadyl oxalate (IV), vanadyl sulfate (IV), oxobis(1-phenyl-1,3-butanedionate)vanadium (IV), bis(maltolato)oxovanadium (IV), vanadium pentoxide (V), sodium metavanadate (V) and ammon metavanadate (V).

Photopolymerization Initiators

As the photopolymerization initiator, the following compounds can be used in a single kind or in two or more kinds in combination.

Acylphosphinoxide Derivatives:
2,4,6-Trimethylbenzoyldiphenylphosphinoxide,
2,6-Dimethoxybenzoyldiphenylphosphinoxide,
2,6-Dichlorobenzoyldiphenylphosphinoxide,
Methyl ester of 2,4,6-trimethylbenzoylphenyl phosphinic acid,
2-Methylbenzoyldiphenylphosphinoxide,
Isopropyl ester of piveroylphenyl phosphinic acid,
Bis-(2,6-dichlorobenzoyl)phenylphosphinoxide,
Bis-(2,6-dichlorobenzoyl)-2,5-dimethylphenylphosphinoxide,
Bis-(2,6-dichlorobenzoyl)-4-propylphenylphosphinoxide,
Bis-(2,6-dichlorobenzoyl)-1-naphthylphosphinoxide,
Bis-(2,6-dimethoxybenzoyl)phenylphosphinoxide,
Bis-(2,6-dimethoxybenzoyl)-2,4,4-trimethylpentylphosphinoxide,
Bis-(2,6-dimethoxybenzoyl)-2,5-dimethylphenylphosphinoxide,
Bis-(2,4,6-trimethylbenzoyl)phenylphosphinoxide, and
Bis-(2,5,6-trimethylbenzoyl)-2,4,4-trimethylpentylphosphinoxide.

α-Diketones:
Diacetyl,
Acetylbenzoyl,
Benzyl,
2,3-Pentadion,
2,3-Octadion,
4,4'-Dimethoxybenzyl,
4,4'-Oxybenzyl,
Camphorquinone,
9,10-Phenanthrenequinone, and
Acenaphthenequinone.

Benzoinalkyl Ethers:
Benzoin methyl ether,
Benzoin ethyl ether, and
Benzoin propyl ether.

Thioxanthone Derivatives:
2,4-Diethoxythioxanthone,
2-chlorothioxanthone, and
Methylthioxanthone.

Benzophenone Derivatives:
Benzophenone,
p,p'-Dimethylaminobenzophenone, and
p,p'-Methoxybenzophenone.

Among the above photopolymerization initiators, it is desired to use α-diketone from the standpoint of polymerization activity and low level of benefit or harm to the living body. When the α-diketone is to be used, further, it is desired to use a tertiary amine compound in combination. As the tertiary amine compound that can be used in combination with the α-diketone, there can be exemplified the following compounds.

Tertiary Amine Compounds:
N,N-Dimethylaniline,
N,N-diethylaniline,
N,N-di-n-butylaniline,
N,N-dibenzylaniline,
N,N-dimethyl-p-toluidine,
N,N-diethyl-p-toluidine,
N,N-dimethyl-m-toluidine,
p-Bromo-N,N-dimethylaniline,
m-Chloro-N,N-dimethylaniline,
p-Dimethylaminobenzaldehyde,
p-Dimethylaminoacetophenone,
p-Dimethylaminobenzoic acid,
Ethyl p-dimethylaminobenzoate,
Amyl p-dimethylaminobenzoate,
Methyl N,N-dimethylanthranilate,
N,N-dihydroxyethylaniline,
N,N-dihydroxyethyl-p-toluidine,
p-Dimethylaminophenetyl alcohol,
p-Dimethylaminostilbene,
N,N-dimethyl-3,5-xylydine,
4-Dimethylaminopyridine,
N,N-dimethyl-α-naphthylamine,
N,N-dimethyl-β-naphthylamine,
Tributylamine,
Tripropylamine,
Triethylamine,
N-methyldiethanolamine,
N-ethyldiethanolamine,
N,N-dimethylhexylamine,
N,N-dimethyldodecylamine,
N,N-dimethylstearylamine,
N,N-dimethylaminoethyl methacrylate,
N,N-diethylaminoethyl methacrylate, and
2,2'-(n-Butylimino)diethanol.

Not only being used in a single kind, the above various kinds of polymerization initiators can also be used in a plurality of kinds in combination, as required.

In the present invention, there is no particular limitation on the amount of blending the polymerization initiators provided the monomer component (A) comprising the above-mentioned radically polymerizable monomer can be polymerized and cured. The amount of blending the polymerization initiators may be suitably selected in a customary manner depending upon the kinds thereof and the composition of the monomer component (A). In general, the blending amount is 0.01 to 30 parts by mass and, particularly, 0.1 to 5 parts by mass per 100 parts by mass of the monomer component (A). When the radically polymerizable compound is used as a component of the polymerization initiator like the above-mentioned acidic group-containing radically polymerizable monomer, however, the above compound is contained in the monomer component (A) and, hence, the amount of the polymerization initiator other than the above compound is selected to lie within the above-mentioned range.

<Water-Soluble Polymers (Component E)>

In the present invention, further, the water-soluble polymers may be blended in addition to the above-mentioned components (A) to (D) to thereby greatly decrease the formation of the unpolymerized product on the surfaces of the cured body. That is, the water-soluble polymer dissolves in water and is distributed together with the surfactant in the water layer formed on the surfaces of the cured body. It is therefore considered that the water layer exhibits an enhanced oxygen shut-off property accounting for a markedly improved effect for suppressing the formation of the unpolymerized product.

In the present invention, the water-soluble polymer stands for the one that exhibits a solubility in water at 23° C. of not smaller than 1 g/liter.

Examples of the water-soluble polymer include polyvinyl alcohol, polyvinyl pyrrolidone, polyethylene oxide, cellulose derivative, polyacrylic acid, polymethacrylic acid, sodium polyacrylate, sodium polymethacrylate, gelatin, copolymer of alkylvinyl ether and maleic anhydride, vinyl acetate/acrylic copolymer, vinyl acetate/ethylene copolymer, acrylic/styrene copolymer, urethane resin and vinylidene chloride resin. Among them, it is particularly desired to use polyvinyl alcohol and polyacrylic acid from the standpoint of further decreasing the effect of oxygen at the time of curing. The water-soluble polymers can be used in a single kind or in two or more kinds in combination.

There is no particular limitation on the water-soluble polymer provided the solubility thereof in water lies within the above-mentioned range. However, a too great molecular weight results in a high viscosity of the curable composition often causing the operability to decrease. Therefore, the weight average molecular weight is desirably 1000 to 10,000,000 and, particularly, 3000 to 500,000 calculated as a polystyrene.

In the present invention, it is desired that the amount of blending the water-soluble polymer is 0.00001 to 10 parts by mass, particularly preferably, 0.0001 to 1 part by mass and, most desirably, 0.0005 to 0.5 parts by mass per 100 parts by mass of the monomer component (A). Formation of the unpolymerized layer on the surfaces can be decreased with an increase in the blending amount thereof but the properties are less affected when the blending amount thereof is small.

<Other Blended Components>

The curable composition of the present invention can be used in its form for imparting luster to the surfaces of various resin-type dental materials, or can be used as a dental restorative such as a surface lustering material or an adhesive used for manicuring the teeth or for repairing the teeth of which the color has changed, and can be used in a more wide range of applications upon being combined with a filler. When used in combination with an organic filler, for example, the curable composition of the invention can be preferably used as a material for repairing denture, as a material for back lining, as a false sealing material or a temporary crown filled in a cavity for several days before a patient go home after the therapy until he visits again for therapy, and as a material for preparing a bridge. When used in combination with an inorganic filler, further, the curable composition of the invention can be preferably used as a dental restorative, such as composite resin, indirect composite resin, inlay, onlay and crown.

Described below are representative examples of the organic filler and the inorganic filler which can be preferably used in a single kind or in two or more kinds in combination.

Organic Fillers:
Polymethylmethacrylate, polyethylmethacrylate, methyl methacrylate/ethyl methacrylate copolymer, crosslinked polymethylmethacrylate, crosslinked polyethylmethacrylate, ethylene/vinyl acetate copolymer, styrene/butadiene copolymer, acrylonitrile/styrene copolymer and acrylonitrile/styrene/butadiene copolymer.

Inorganic Fillers:
Quartz, silica, alumina, silica-titania, silica-zirconia, lanthanum glass, barium glass and strontium glass.

In addition to those exemplified above, the inorganic fillers may be those that are cationically soluble like hydroxides such as calcium hydroxide and strontium hydroxide, or oxides such as zinc oxide, glass silicate or fluoroaluminosilicate glass, which may be used in one kind or in two or more kinds being mixed together. There can be further used a granular organic-inorganic composite filler obtained by adding a polymerizable monomer to the above inorganic filler to obtain a mixture thereof in the form of a paste which is, then, polymerized and milled.

Though there is no particular limitation on the particle size of the above fillers, the fillers that are usually preferably used as a dental material have an average particle size in a range of 0.01 µm to 100 µm. There is no particular limitation, either, on the refractive index of the filler. The fillers having refractive indexes in a range of 1.4 to 1.7 as possessed by dental fillers, in general, can be used without limitation.

Further, the curable composition blended with a spherical inorganic filler among the above-mentioned fillers works to improve the surface luster of the cured body that is obtained, and can be used as an excellent dental restorative.

It is desired that the above inorganic filler is treated with a surface-treating agent as represented by a silane coupling agent from the standpoint of improving affinity to the polymerizable monomer and enhancing the mechanical strength and resistance against the water. The surface treatment may be conducted in a customary manner by using a silane coupling agent, such as methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy)silane, γ-methacryloyloxypropyltrimethoxysilane, γ-chloropropyltrimethoxysilane, γ-glycidoxypropyltrimethoxysilane and hexamethyldisilazane.

The amount of blending the above various fillers may be suitably determined depending upon the use by taking into consideration the viscosity (operability) of when it is mixed with the polymerizable monomer and the mechanical properties of the cured body. Generally, however, the fillers are blended in an amount in a range of 50 to 1500 parts by mass and, particularly, 70 to 1000 parts by mass per 100 parts by mass of the monomer component (A).

In addition to the above-mentioned fillers, the curable composition of the present invention may further be blended with a coloring material such as a pigment or a fluorescent pigment to be in match in color tone with the teeth or the gum, or may be blended with an ultraviolet ray absorber for preventing discoloration caused by ultraviolet rays. To improve preservation stability, further, the curable composition of the present invention may be blended with a polymerization inhibitor.

<Curable Compositions>

The curable composition of the present invention is prepared by homogeneously mixing the above-mentioned components together and by dispersing, in the monomer component (A), the components (B) to (D) and, as required, the water-soluble polymer of the component (E) as well as any other components, and is suitably heated or irradiated with light depending upon the kind of the polymerization initiator (D) so as to be polymerized and cured, thereby to obtain a cured body.

By taking stability during the preservation into consideration, further, the curable composition of the invention may be cold-preserved at a temperature of about 0 to 10° C., and may be polymerized and cured by returning it back to room temperature when it is to be used. In particular, the curable composition blended with the anionic surfactant (c-1) and the nonionic surfactant (c-2) in combination as a surfactant (C) can be favorably cold-preserved as described earlier, making it possible to effectively avoid a drop in the properties caused by the precipitation of anionic surfactants.

Further, the curable composition may be preserved being divided into two or more components so that the curing will not take place until when it is to be used, and the divided components may all be mixed together at the time of use so as to be polymerized and cured.

Further, the polymerization and curing are conducted in a state where there is present water which is the above-mentioned component (B). Therefore, the unpolymerized product is effectively suppressed from being formed on the surfaces of the cured body even when the polymerization and curing take place in a state where the surfaces are at least partly opened to the atmosphere (oxygen atmosphere) effectively avoiding a drop in the hardness and strength caused by the formation of the unpolymerized product. Therefore, while the curable composition of the present invention is very useful as a dental restorative, it can also be utilized for industrial uses in general.

EXAMPLES

The invention will now be concretely described by way of Examples to which only, however, the invention is in no way limited.

Described below are the compounds used in Examples and in Comparative Examples, their abbreviations, and the methods of evaluating the curable compositions that are prepared.

[Radically Polymerizable Monomers]

AAEM: Acetoacetoxyethyl methacrylate (water absorbing capacity: 1.4% by weight)

HD: 1,6-Hexanediol dimethacrylate (water absorbing capacity: 0.1% by weight)

bis-GMA: 2,2-Bis(4-(2-hydroxy-3-methacryloyloxypropoxy)phenyl)propane (water absorbing capacity: 2.2% by weight)

3G: Triethylene glycol dimethacrylate (water absorbing capacity: 1.7% by weight)

D2.6E: 2,2-Bis(4-methacryloyloxypolyethoxyphenyl)propane (water absorbing capacity: 0.3% by weight)

HEMA: Hydroxyethyl methacrylate (water absorbing capacity: >100% by weight)

14G: Dimethacrylate of polyethylene glycol having a molecular weight of 600 (water absorbing capacity: >100% by weight)

MAC-10: 11-Methacryloyloxy-1,1-undecanedicarboxylic acid (water absorbing capacity: 0.6% by weight)

PM: A mixture of 2-methacryloyloxyethyldihydrogen Phosphate and bis(2-methacryloyloxyethyl)hydrogen phosphate (water absorbing capacity: >100% by weight)

[Anionic Surfactants]

SLS: Sodium lauryl sulfate (HLB: 40)
SDS: Sodium decyl sulfate (HLB: 41)
SOS: Sodium octane sulfonate
LBS: Sodium laurylbenzene sulfonate

[Cationic Surfactants]

LDAGCl: Hydrochloric acid lauryldiaminoethyl glycine (HLB: 30)
LTMACl: Lauryltrimethylammonium chloride (HLB: 11)

[Nonionic Surfactants]

POEL: Polyoxyethylene (10) lauryl ether (HLB: 14)
POEL4: Polyoxyethylene (4) lauryl ether (HLB: 10)
POEO2: Polyoxyethylene (2) oleyl ether (HLB: 8)
POEO7: Polyoxyethylene (7) oleyl ether (HLB: 11)
POEO15: Polyoxyethylene (15) oleyl ether (HLB: 16)

[Polymerization Initiators]

(Organic Peroxides)
BPO: Benzoyl peroxide
Perocta H: 1,1,3,3-Tetramethylbutylhydro peroxide (Amine Compounds)
DEPT: N,N-Diethanol-p-toluidine
DMPT: N,N-dimethyl-p-toluidine
PEAT: N,N-Diethyl-p-toluidine
DMBE: Ethyl dimethylbenzoate ($\alpha$-Diketones)
CQ: Camphorquinone (Aryl borate Compounds)
phBTEOA: Tetraphenylboron triethanolamine salt (Vanadium Compounds)
VOAA: Vanadium oxide (IV) acetylacetonato

[Water-soluble polymers]

PVA1000: Polyvinyl alcohol (completely saponified product, average polymerization degree of 1000, average molecular weight of 50000)

[Fillers]

3Si—Zr: γ-Methacryloyloxypropyltrimethoxysilane of which the surface is treated of amorphous silica-zirconia, (average particle size: 3 μm)

0.3Si—Ti: γ-Methacryloyloxypropyltrimethoxysilane of which the surface is treated of spherical silica-titania (average particle size: 0.3 μm)

PEMA: Polyethyl methacrylate (average particle size: 30 μm)

[Method of Measuring the Water Absorbing Capacity]

A radically polymerizable monomer (or a mixture thereof) was mixed with water at 23° C., the content of water in the monomer that has absorbed the water to a saturation was measured by the Karl Fischer's method (Model, CA-02 manufactured by Mitsubishi Kagaku Co.), and the water absorbing capacity was found according to the following formula, $$\text{Water absorbing capacity} = [\text{water content }(g)/\text{weight }(g)\text{ of monomer (or a mixture thereof)}] \times 100$$

[Method of Measuring the Amount of Unpolymerized Product on the Surfaces]

A curable composition prepared in Example or in Comparative Example was filled in a polyacetal mold having a hole of a diameter of 50 mm and a thickness of 1 mm, and was left in a constant-temperature bath under a wet condition at 37° C. for 15 minutes to effect the curing. In Examples 19 to 23 and in Comparative Examples 16 to 20, however, the curing was effected by the irradiation with light for 30 seconds by using a visible light irradiator (Power-Light manufactured by Tokuyama Co.).

Thereafter, the surfaces of the obtained cured body was washed with ethanol to remove the unpolymerized layer. The amount of the unpolymerized product was found by subtracting the weight of the cured body without unpolymerized layer from the weight of the curable composition filled in the mold, and was regarded to be the weight per the surface area.

[Method of Measuring the Bending Strength]

A curable composition was filled in the polyacetal mold having a rectangular hole of a width of 4 mm, a thickness of 2 mm and a length of 40 mm, and was cured in the same manner as in the case of measuring the amount of the unpolymerized product.

The obtained cured product was subjected to the three-point bending test by using a strength tester (Autograph, manufactured by Shimazu Seisakusho Co.) under the conditions of a crosshead speed of 1 mm/min. and a span distance of 15 mm to find the bending strength.

Further, the surface hardness of the cured body was measured in accordance with ADAS No. 17 (Denture Base Temporary Relining Resins).

[Evaluation of Polishing/Grinding Properties]

A curable composition was filled in the polyacetal mold having a square hole of a width of 10 mm and a thickness of 2 mm, and was cured in the same manner as in the case of measuring the amount of the unpolymerized product.

A dental carbide bur (Hardi-Alloy Bur DD6 manufactured by Tokuyama Co.) was attached to a dental motor hand piece (micro-motor, ANS 3000 manufactured by Morita Co.), and the obtained cured body was measured for its polishing and grinding properties on the surfaces thereof. The standards for evaluation were as follows:

○: Unpolymerized layer does not get entangled with the carbide bur.

X: Unpolymerized layer gets entangled with the carbide bur.

[Preservation Stability Testing]

The curable composition was preserved in a refrigerator maintained at 4° C. for one week, and was examined concerning the precipitation of surfactants for evaluation on the basis of the following two steps.

○: Surfactant is not precipitating.

X: Surfactant is precipitating.

Example 1

By using the 3G having a water absorbing capacity of 1.7% by weight as a polymerizable monomer, there were prepared a first liquid and a second liquid according to following the recipes.

Recipe for the First Liquid:
3G (monomer component (A)): 100 parts by mass
Water: 3 parts by mass
SLS (anionic surfactant): 1.5 parts by mass
BPO (organic peroxide): 3 parts by mass Recipe for the Second Liquid:
3G (monomer component (A)): 100 parts by mass
Water: 3 parts by mass
SLS (anionic surfactant): 1.5 parts by mass
DMPT (amine compound): 1.5 parts by mass The first liquid and the second liquid having the above compositions were mixed together to prepare a curable composition described below.

Curable Composition:
3G (monomer component (A)): 100 parts by mass
Water: 3 parts by mass
SLS (surfactant): 1.5 parts by mass
BPO (organic peroxide): 1.5 parts by mass
DMPT (amine compound): 0.75 parts by mass The curable composition was evaluated for its properties by the methods described above. As a result, the content of the unpolymerized product on the surfaces was 6 μg/mm$^2$ and the bending strength of the cured body was 80 MPa.

Examples 2 to 5

Curable compositions were prepared in the same manner as in Example 1 but changing the kinds of the surfactants that were used as shown in Table 1, and were evaluated for their amounts of unpolymerized product on the surfaces. Table 1 shows the results thereof together with the results of Example 1.

Comparative Example 1

A curable composition shown in Table 1 was prepared in quite the same manner as in Example 1 but using neither the water nor the surfactant.

As a result, the amount of the unpolymerized product on the surfaces was 730 μg/mm$^2$. The bending strength of the cured body was 83 MPa.

Comparative Examples 2 and 3

Curable compositions shown in Table 1 were prepared in the same manner as in Example 1, and were measured for their amounts of unpolymerized product on the surfaces. The results were as shown in Table 1.

TABLE 1

| | Polymerizable monomer* Monomer component (A) | | Water | Surfactant | | Polymerization initiator | Unpolymerized product on |
|---|---|---|---|---|---|---|---|
| | Kind | Amount (Mass pts) | Amount (Mass pts) | Kind | Amount (Mass pts) | BPO/DMPT (Mass pts) | surface (μg/mm$^2$) |
| Ex. 1 | 3G | 100 | 3 | SLS | 1.5 | 1.5/0.75 | 6 |
| Ex. 2 | 3G | 100 | 3 | SDS | 1.5 | 1.5/0.75 | 5 |

TABLE 1-continued

| | Polymerizable monomer* Monomer component (A) | | Water | Surfactant | | Polymerization initiator | Unpolymerized product on |
|---|---|---|---|---|---|---|---|
| | Kind | Amount (Mass pts) | Amount (Mass pts) | Kind | Amount (Mass pts) | BPO/DMPT (Mass pts) | surface (µg/mm²) |
| Ex. 3 | 3G | 100 | 3 | LDAGCl | 1.5 | 1.5/0.75 | 18 |
| Ex. 4 | 3G | 100 | 3 | LTMACl | 1.5 | 1.5/0.75 | 58 |
| Ex. 5 | 3G | 100 | 3 | POEL | 1.5 | 1.5/0.75 | 56 |
| Comp. Ex. 1 | 3G | 100 | — | — | — | 1.5/0.75 | 730 |
| Comp. Ex. 2 | 3G | 100 | 3 | — | — | 1.5/0.75 | 580 |
| Comp. Ex. 3 | 3G | 100 | — | SLS | 1.5 | 1.5/0.75 | 730 |

*A water absorbing capacity is 1.7% by weight

Example 6

A curable composition shown in Table 2 was prepared in the same manner as in Example 1 but using the HD having a water absorbing capacity of 0.1% by weight as a polymerizable monomer, and was measured for its amount of the unpolymerized product on the surfaces. As a result, the amount of the unpolymerized product on the surfaces was 7 µg/mm² (Table 2 also shows the measured amount of the unpolymerized product on the surfaces).

Comparative Example 4

A curable composition shown in Table 2 was prepared in quite the same manner as in Example 6 but using neither the water nor the surfactant, and was measured for its amount of the unpolymerized product on the surfaces.

As a result, the amount of the unpolymerized product on the surfaces was 512 µg/mm² (Table 2 also shows the measured amount of the unpolymerized product on the surfaces).

Example 7

A curable composition was prepared in the same manner as in Example 1 but using the AAEM having a water absorbing capacity of 1.4% by weight as a polymerizable monomer, and was measured for its amount of the unpolymerized product on the surfaces. As a result, the amount of the unpolymerized product on the surfaces was 32 µg/mm² (Table 2 also shows the measured amount of the unpolymerized product on the surfaces).

Example 8

A mixture of polymerizable monomers, i.e., 95 parts by mass of AAEM and 5 parts by mass of HEMA was prepared. The mixture of the polymerizable monomers was measured for its water absorbing capacity to be 2.9% by weight.

A curable composition was prepared in the same manner as in Example 1 but using the above mixture instead of the 3G, and was measured for its amount of the unpolymerized product on the surfaces.

As a result, the amount of the unpolymerized product on the surfaces was 6 µg/mm² (Table 2 also shows the measured amount of the unpolymerized product on the surfaces).

Comparative Example 5

A curable composition shown in Table 2 was prepared in quite the same manner as in Example 7 by using the AAEM as a polymerizable monomer but using neither the water nor the surfactant, and was measured for its amount of the unpolymerized product on the surfaces. As a result, the amount of the unpolymerized product on the surfaces was 652 µg/mm² (Table 2 also shows the measured amount of the unpolymerized product on the surfaces).

Examples 9 to 11, Comparative Examples 6 to 9

Curable composition shown in Table 2 were prepared in the same manner as in Example 1 by using mixtures of polymerizable monomers, i.e., mixtures of AAEM and HEMA, and were measured for their amounts of unpolymerized product on the surfaces. Table 2 also shows the evaluated results of the water absorbing capacities of the mixtures of polymerizable monomers and of the amounts of unpolymerized product on the surfaces.

TABLE 2

| | Polymerizable monomer (monomer component A) | | | Water | Surfactant | | Polymerization | Unpolymerized |
|---|---|---|---|---|---|---|---|---|
| | Kind | Blending amount (mass pts) | Water absorbing capacity | Blending amount (mass pts) | Kind | Blending amount (mass pts) | initiator BPO/DMPT (mass pts) | product on surface (µg/mm²) |
| Example 6 | HD | 100 | 0.1 wt % | 3 | SLS | 1.5 | 1.5/0.75 | 7 |
| Example 7 | AAEM HEMA | 100 — | 1.4 wt % | 3 | SLS | 1.5 | 1.5/0.75 | 32 |

TABLE 2-continued

|  | Polymerizable monomer (monomer component A) | | | Water | Surfactant | | Polymerization initiator BPO/DMPT (mass pts) | Unpolymerized product on surface (μg/mm²) |
|---|---|---|---|---|---|---|---|---|
|  | Kind | Blending amount (mass pts) | Water absorbing capacity | Blending amount (mass pts) | Kind | Blending amount (mass pts) | | |
| Example 8 | AAEM | 95 | 2.9 wt % | 3 | SLS | 1.5 | 1.5/0.75 | 6 |
|  | HEMA | 5 | | | | | | |
| Example 9 | AAEM | 70 | 10.3 wt % | 3 | SLS | 1.5 | 1.5/0.75 | 12 |
|  | HEMA | 30 | | | | | | |
| Example 10 | AAEM | 50 | 16.4 wt % | 3 | SLS | 1.5 | 1.5/0.75 | 52 |
|  | HEMA | 50 | | | | | | |
| Example 11 | AAEM | 50 | 16.4 wt % | 5 | SLS | 1.5 | 1.5/0.75 | 8 |
|  | HEMA | 50 | | | | | | |
| Comparative Example 4 | HD | 100 | 0.1 wt % | — | — | — | 1.5/0.75 | 512 |
| Comparative Example 5 | AAEM | 100 | 1.4 wt % | — | — | — | 1.5/0.75 | 652 |
|  | HEMA | — | | | | | | |
| Comparative Example 6 | AAEM | 95 | 2.9 wt % | — | — | — | 1.5/0.75 | 644 |
|  | HEMA | 5 | | | | | | |
| Comparative Example 7 | AAEM | 70 | 10.3 wt % | — | — | — | 1.5/0.75 | 638 |
|  | HEMA | 30 | | | | | | |
| Comparative Example 8 | AAEM | 50 | 16.4 wt % | — | — | — | 1.5/0.75 | 562 |
|  | HEMA | 50 | | | | | | |
| Comparative Example 9 | AAEM | 20 | 28.3 wt % | 3 | SLS | 1.5 | 1.5/0.75 | 521 |
|  | HEMA | 80 | | | | | | |

Examples 12 to 15, Comparative Examples 10 and 11

Curable compositions shown in Table 3 were prepared in the same manner as in Example 1 but changing the amounts of blending the water and the surfactant, and were evaluated for their amounts of unpolymerized product on the surfaces and the bending strength. Table 3 shows the results thereof together with the results of Example 1.

TABLE 3

|  | Polymerizable monomer* | | Water | Surfactant | | Polymerization initiator BPO/DMPT (mass pts) | Unpolymerized product on surface (μg/mm²) | Blending strength |
|---|---|---|---|---|---|---|---|---|
|  | Kind | Blending amount (mass pts) | Blending amount (mass pts) | Kind | Blending amount (mass pts) | | | |
| Example 1 | 3G | 100 | 3 | SLS | 1.5 | 1.5/0.75 | 6 | 80 MPa |
| Example 12 | 3G | 100 | 1 | SLS | 1.5 | 1.5/0.75 | 38 | 82 MPa |
| Example 13 | 3G | 100 | 5 | SLS | 1.5 | 1.5/0.75 | 4 | 76 MPa |
| Example 14 | 3G | 100 | 3 | SLS | 1 | 1.5/0.75 | 9 | 79 MPa |
| Example 15 | 3G | 100 | 3 | SLS | 2 | 1.5/0.75 | 5 | 79 MPa |
| Comparative Example 10 | 3G | 100 | 0.1 | SLS | 1.5 | 1.5/0.75 | 630 | 83 MPa |
| Comparative Example 11 | 3G | 100 | 20 | SLS | 1.5 | 1.5/0.75 | 52 | 39 MPa |

*3G has a water absorbing capacity of 1.7% by weight.

Examples 16 to 18, Comparative Examples 12 to 15

Curable compositions shown in Table 4 were prepared in the same manner as in Example 1 but using mixtures of monomers of compositions shown in Table 4 and changing the amounts of blending the water and the surfactant, and were evaluated for their amounts of polymerized product on the surfaces and the bending strengths. Table 4 shows the results thereof together with the results of Example 1.

Cured bodies were prepared in the same manner as in Example 1 but changing the amounts of blending the water and the surfactant so that the compositions thereof were as shown in Table 4, and were evaluated. Table 4 shows the evaluated results of the amounts of the unpolymerized product on the surfaces together with the results of Example 1. Table 4 further shows water absorbing capacities of the mixtures of the monomers that were used.

TABLE 4

| | Polymerizable monomer (monomer component A) | | | Water | Surfactant | | Polymerization initiator | Unpolymerized |
| --- | --- | --- | --- | --- | --- | --- | --- | --- |
| | Kind | Blending amount (mass pts) | Water absorbing capacity | Blending amount (mass pts) | Kind | Blending amount (mass pts) | (mass pts) BPO/DMPT (mass pts) | product on surface (μg/mm$^2$) |
| Example 1 | 3G | 100 | 1.7 wt % | 3 | SLS | 1.5 | 1.5/0.75 | 6 |
| Example 16 | 3G | 90 | 2.4 wt % | 3 | SLS | 1.5 | 1.5/0.75 | 1 |
| | 14G | 10 | | | | | | |
| Example 17 | 3G | 70 | 5.3 wt % | 3 | SLS | 1.5 | 1.5/0.75 | 2 |
| | 14G | 30 | | | | | | |
| Example 18 | 3G | 95 | 2.9 wt % | 3 | SLS | 1.5 | 1.5/0.75 | 2 |
| | HEMA | 5 | | | | | | |
| Comparative Example 12 | 3G | 99.9 | 1.8 wt % | 3 | SLS | 1.5 | 1.5/0.75 | 6 |
| | 14G | 0.1 | | | | | | |
| Comparative Example 13 | 3G | 30 | 23.2 wt % | 3 | SLS | 1.5 | 1.5/0.75 | 612 |
| | 14G | 70 | | | | | | |
| Comparative Example 14 | 3G | 99.9 | 1.8 wt % | 3 | SLS | 1.5 | 1.5/0.75 | 6 |
| | HEMA | 0.1 | | | | | | |
| Comparative Example 15 | 3G | 30 | 25.3 wt % | 3 | SLS | 1.5 | 1.5/0.75 | 566 |
| | HEMA | 70 | | | | | | |

Examples 19 and 20, Comparative Examples 16 and 17

Visible light-curable compositions shown in Table 5 were prepared under the conditions of shutting off the light. The curable compositions were cured by the irradiation with light by using a visible light irradiator to obtain cured bodies thereof, and were evaluated for their amounts of unpolymerized product on the surfaces, hardness and polishing/grinding properties thereof on the basis of the above-mentioned evaluation methods. The results were as shown in Table 5 which also shows water absorbing capacities of the mixtures of polymerizable monomers.

Examples 21 and 22, Comparative Examples 18 and 19

Two compositions A and B were prepared as shown in Table 5, and were mixed together to prepare curable compositions. The curable compositions were cured by the irradiation with light, and were evaluated for their amounts of unpolymerized product on the surfaces of the cured bodies, hardness and polishing/grinding properties thereof in the same manner as in Example 19. The results were as shown in Table 5 which also shows water absorbing capacities of the mixtures of polymerizable monomers used for the preparation of the two compositions.

TABLE 5

| | | Polymerizable monomer (monomer component A) | | | Water | Surfactant | | Polymerization initiator | | Filler | | | | |
| --- | --- | --- | --- | --- | --- | --- | --- | --- | --- | --- | --- | --- | --- | --- |
| | | Kind | Blending amount (mass pts) | Water absorbing capacity | Blending amount (mass pts) | Kind | Blending amount (mass pts) | Kind | Blending amount (mass pts) | Kind | Blending amount (mass pts) | Unpolymerized product on surface | Hardness | Polishing/ grinding property |
| Example 19 | | Bis-GMA | 70 | 0.3 wt % | 3 | SLS | 1.5 | CQ | 0.07 | 3Si—Zr | 150 | 7 μg/mm$^2$ | 24 | ○ |
| | | 3G | 30 | | | | | DMBE | 0.08 | 0.3Si—Zr | 150 | | | |
| Example 20 | | Bis-GMA | 56 | 2.5 wt % | 3 | SLS | 1.5 | CQ | 0.07 | 3Si—Zr | 150 | 1 μg/mm$^2$ | 23 | ○ |
| | | 3G | 24 | | | | | DMBE | 0.08 | 0.3Si—Zr | 150 | | | |
| | | 14G | 20 | | | | | | | | | | | |
| Example 21 | A | Bis-GMA | 20 | 0.3 wt % | 1.5 | SLS | 0.75 | DEPT | 0.5 | 3Si—Zr | 75 | 9 μg/mm$^2$ | 20 | ○ |
| | | 3G | 30 | | | | | | | 0.3Si—Zr | 75 | | | |
| | B | Bis-GMA | 20 | | 1.5 | SLS | 0.75 | BPO | 1.5 | 3Si—Zr | 75 | | | |
| | | 3G | 30 | | | | | | | 0.3Si—Zr | 75 | | | |
| Example 22 | A | Bis-GMA | 16 | 2.8 wt % | 1.5 | SLS | 0.75 | DEPT | 0.5 | 3Si—Zr | 75 | 3 μg/mm$^2$ | 19 | ○ |
| | | 3G | 24 | | | | | | | 0.3Si—Zr | 75 | | | |
| | | 14G | 10 | | | | | | | | | | | |
| | B | Bis-GMA | 16 | | 1.5 | SLS | 0.75 | BPO | 1.5 | 3Si—Zr | 75 | | | |
| | | 3G | 24 | | | | | | | 0.3Si—Zr | 75 | | | |
| | | 14G | 10 | | | | | | | | | | | |
| Comp. Example 16 | | Bis-GMA | 70 | 0.3 wt % | — | SLS | — | CQ | 0.07 | 3Si—Zr | 150 | 568 μg/mm$^2$ | 10 | X |
| | | 3G | 30 | | | | | DMBE | 0.08 | 0.3Si—Zr | 150 | | | |
| Comp. Example 17 | | Bis-GMA | 56 | 2.5 wt % | — | SLS | — | CQ | 0.07 | 3Si—Zr | 150 | 553 μg/mm$^2$ | 9 | X |
| | | 3G | 24 | | | | | DMBE | 0.08 | 0.3Si—Zr | 150 | | | |
| | | 14G | 20 | | | | | | | | | | | |

TABLE 5-continued

| | | Polymerizable monomer (monomer component A) | | | Water | Surfactant | | Polymerization initiator | | Filler | | | | |
|---|---|---|---|---|---|---|---|---|---|---|---|---|---|---|
| | | Kind | Blending amount (mass pts) | Water absorbing capacity | Blending amount (mass pts) | Kind | Blending amount (mass pts) | Kind | Blending amount (mass pts) | Kind | Blending amount (mass pts) | Unpolymerized product on surface | Hardness | Polishing/grinding property |
| Comp. Example 18 | A | Bis-GMA 3G | 20 30 | 0.3 wt % | — | SLS | — | DEPT | 0.5 | 3Si—Zr 0.3Si—Zr | 75 75 | 620 µg/mm² | 8 | X |
| | B | Bis-GMA 3G | 20 30 | | | SLS | — | BPO | 1.5 | 3Si—Zr 0.3Si—Zr | 75 75 | | | |
| Comp. Example 19 | A | Bis-GMA 3G 14G | 16 24 10 | 2.9 wt % | — | SLS | — | DEPT | 0.5 | 3Si—Zr 0.3Si—Zr | 75 75 | 610 µg/mm² | 7 | X |
| | B | Bis-GMA 3G 14G | 16 24 10 | | | SLS | — | BPO | 1.5 | 3Si—Zr 0.3Si—Zr | 75 75 | | | |

Example 23, Comparative Example 20

Two compositions A and B were prepared as shown in Table 6, and were mixed together to prepare curable compositions. The curable compositions were cured by the irradiation with light, and were evaluated for their amounts of unpolymerized product on the surfaces of the cured bodies, hardness and polishing/grinding properties thereof in the same manner as in Example 19. The results were as shown in Table 6. Mixtures of polymerizable monomers were further separately prepared according to the ratios of blending the polymerizable monomers in the curable compositions shown in Table 6, and were measured for their water absorbing capacities. The results were as shown in Table 6.

SLS (anionic surfactant): 1.5 parts by mass
POEL4 (nonionic surfactant): 1.5 parts by mass
BPO (organic peroxide): 3 parts by mass Recipe for the Second Liquid:
3G (monomer component (A)): 100 parts by mass
Water: 3 parts by mass
SLS (anionic surfactant): 1.5 parts by mass
POEL4 (nonionic surfactant): 1.5 parts by mass
DMPT (amine compound): 1.5 parts by mass The first liquid and the second liquid having the above compositions were mixed together to prepare a curable composition described below.

TABLE 6

| | | Polymerizable monomer (monomer component A) | | | Water | Surfactant | | Polymerization initiator | | Filler | | | | |
|---|---|---|---|---|---|---|---|---|---|---|---|---|---|---|
| | | Kind | Blending amount (mass pts) | Water absorbing capacity | Blending amount (mass pts) | Kind | Blending amount (mass pts) | Kind | Blending amount (mass pts) | Kind | Blending amount (mass pts) | Unpolymerized product on surface | Hardness | Polishing/grinding property |
| Example 23 | A | Bis-GMA 3G HEMA | 15 30 5 | 2.9 wt % | 1.5 | SLS | 0.75 | PhBTEOA p-octaH | 3 0.75 | 3Si—Zr 0.3Si—Zr | 75 75 | .12 µg/mm² | 17 | ○ |
| | B | PM MAC-10 D-2.6E 3G | 15 2.5 22.5 10 | | 1.5 | SLS | 0.75 | VOAA | 0.125 | 3Si—Zr 0.3Si—Zr | 75 75 | | | |
| Comp. Example 20 | A | Bis-GMA 3G HEMA | 15 30 5 | 2.9 wt % | — | — | — | PhBTEOA p-octaH | 3 0.75 | 3Si—Zr 0.3Si—Zr | 75 75 | 610 µg/mm² | 6 | X |
| | B | PM MAC-10 D-2.6E 3G | 15 2.5 22.5 10 | | — | — | — | VOAA | 0.125 | 3Si—Zr 0.3Si—Zr | 75 75 | | | |

Example 24

By using the 3G having a water absorbing capacity of 1.7% by weight as a polymerizable monomer, there were prepared a first liquid and a second liquid according to the following recipes.

Recipe for the First Liquid:
3G (monomer component (A)): 100 parts by mass
Water: 3 parts by mass Curable Composition:
3G (monomer component (A)): 100 parts by mass
Water: 3 parts by mass
SLS (surfactant: 1.5 parts by mass
POEL4 (nonionic surfactant): 1.5 parts by mass
BPO (organic peroxide): 1.5 parts by mass
DMPT (amine compound): 0.75 parts by mass The curable composition was evaluated for its amount of unpolymerized product on the surfaces, bending strength and preservation stability (whether the surfactant has precipitated). As a result, the content of the unpolymerized product on the surfaces was 3 µg/mm² and the bending strength of the cured body was 80 MPa. In the preservation stability testing, further, no surfactant has precipitated. Table 7 shows the curable composition, amount of the unpolymerized product on the surfaces and preservation stability.

Examples 25 to 31

Curable compositions were prepared in the same manner as in Example 24 but changing the kinds of the surfactants that were used as shown in Table 7. The obtained curable compositions were evaluated for their amounts of unpolymerized product on the surfaces and the preservation stability. Table 7 shows the results thereof together with the results of Example 1.

The amount of the unpolymerized product on the surfaces was 5 µg/mm², and no surfactant has precipitated in the testing of preservation stability.

Example 33

A mixture of polymerizable monomers, i.e., 70 parts by mass of AAEM and 30 parts by mass of HEMA was prepared. The mixture of the polymerizable monomers was measured for its water absorbing capacity to be 10.3% by weight.

A curable composition was prepared in the same manner as in Example 24 but using the above mixture instead of the 3G, and was measured for its amount of the unpolymerized product on the surfaces and the preservation stability. The results were as shown in Table 8.

The amount of the unpolymerized product on the surfaces was 8 µg/mm², and no surfactant has precipitated in the testing of preservation stability.

TABLE 7

| | Polymerizable monomer* | | Water | Anionic surfactant | | Nonionic surfactant | | Polymerization initiator BPO/DMPT (mass pts) | Unpolymerized product on surface | Precipitation of surfactant |
|---|---|---|---|---|---|---|---|---|---|---|
| | Kind | Blending amount (mass pts) | Blending amount (mass pts) | Kind | Blending amount (mass pts) | Kind | Blending amount (mass pts) | | | |
| Example 24 | 3G | 100 | 3 | SLS | 1.5 | POEL4 | 1.5 | 1.5/0.75 | 3 µg/mm² | ○ |
| Example 25 | 3G | 100 | 3 | SLS | 1.5 | POEL10 | 1.5 | 1.5/0.75 | 4 µg/mm² | ○ |
| Example 26 | 3G | 100 | 3 | SLS | 1.5 | POEO2 | 1.5 | 1.5/0.75 | 4 µg/mm² | ○ |
| Example 27 | 3G | 100 | 3 | SLS | 1.5 | POEO7 | 1.5 | 1.5/0.75 | 4 µg/mm² | ○ |
| Example 28 | 3G | 100 | 3 | SLS | 1.5 | POEO15 | 1.5 | 1.5/0.75 | 4 µg/mm² | ○ |
| Example 29 | 3G | 100 | 3 | SDS | 1.5 | POEL4 | 1.5 | 1.5/0.75 | 3 µg/mm² | ○ |
| Example 30 | 3G | 100 | 3 | SOS | 1.5 | POEL4 | 1.5 | 1.5/0.75 | 3 µg/mm² | ○ |
| Example 31 | 3G | 100 | 3 | LBS | 1.5 | POEL4 | 1.5 | 1.5/0.75 | 7 µg/mm² | ○ |
| Example 1 | 3G | 100 | 3 | SLS | — | — | — | 1.5/0.75 | 5 µg/mm² | — |

*3G has a water absorbing capacity of 1.7% by weight.

Example 32

A curable composition was prepared in the same manner as in Example 24 but using the HD having a water absorbing capacity of 0.1% by weight as a radically polymerizable monomer, and was evaluated for its amount of the unpolymerized product on the surfaces and the preservation stability. The results were as shown in Table 8 which also shows the results of Example 6.

Examples 34 to 36

Curable compositions shown in Table 8 were prepared in the same manner as in Example 24 by using mixtures of polymerizable monomers of AAEM and HEMA, and were measured for their amounts of the unpolymerized product on the surfaces and the preservation stability. The results were as shown in Table 8 which also shows the water absorbing capacities of the mixtures of the polymerizable monomers.

TABLE 8

| | Polymerizable monomer (monomer component A) | | | Water | Anionic surfactant | | Nonionic surfactant | | Polymerization initiator BPO/DMPT (mass pts) | Unpolymerized product on surface | Precipitation of surfactant |
|---|---|---|---|---|---|---|---|---|---|---|---|
| | Kind | Blending amount (mass pts) | Water absorbing capacity | Blending amount (mass pts) | Kind | Blending amount (mass pts) | Kind | Blending amount (mass pts) | | | |
| Example 32 | HD | 100 | 0.1 wt % | 3 | SLS | 1.5 | POEL4 | 1.5 | 1.5/0.75 | 5 µg/mm² | ○ |

TABLE 8-continued

| | Polymerizable monomer (monomer component A) | | | Water | Anionic surfactant | | Nonionic surfactant | | Polymerization | | |
|---|---|---|---|---|---|---|---|---|---|---|---|
| | Kind | Blending amount (mass pts) | Water absorbing capacity | Blending amount (mass pts) | Kind | Blending amount (mass pts) | Kind | Blending amount (mass pts) | initiator BPO/DMPT (mass pts) | Unpolymerized product on surface | Precipitation of surfactant |
| Example 33 | AAEM HEMA | 70 30 | 10.3 wt % | 3 | SLS | 1.5 | POEL4 | 1.5 | 1.5/0.75 | 8 μg/mm$^2$ | ○ |
| Example 34 | AAEM HEMA | 50 50 | 16.4 wt % | 3 | SLS | 1.5 | POEL4 | 1.5 | 1.5/0.75 | 38 μg/mm$^2$ | ○ |
| Example 35 | AAEM HEMA | 50 50 | 16.4 wt % | 5 | SDS | 1.5 | POEL4 | 1.5 | 1.5/0.75 | 6 μg/mm$^2$ | ○ |
| Example 36 | AAEM HEMA | 30 70 | 23.3 wt % | 5 | SLS | 1.5 | POEL4 | 1.5 | 1.5/0.75 | 43 μg/mm$^2$ | ○ |
| Example 6 | HD | 100 | 0.1 wt % | 3 | SLS | 1.5 | — | — | 1.5/0.75 | 7 μg/mm$^2$ | X |

Examples 37 and 38

Curable compositions shown in Table 9 were prepared in the same manner as in Example 24 but changing the amount of blending the water, and were evaluated for their amounts of the unpolymerized product on the surfaces, bending strengths and preservation stability. Table 9 shows the results thereof together with the results of Example 24.

Comparative Example 21

A curable composition was prepared in the same manner as in Example 39 but without at all using any surfactant, and was measured for its amount of the unpolymerized product on the surfaces thereof. The results were as shown in Table 10.

TABLE 9

| | Polymerizable monomer* | | Water | Anionic surfactant | | Nonionic surfactant | | Polymerization initiator BPO/DMPT (mass pts) | Unpolymerized product on surface | Bending strength | Precipitation of surfactant |
|---|---|---|---|---|---|---|---|---|---|---|---|
| | Kind | Blending amount (mass pts) | Blending amount (mass pts) | Kind | Blending amount (mass pts) | Kind | Blending amount (mass pts) | | | | |
| Example 24 | 3G | 100 | 3 | SLS | 1.5 | POEL4 | 1.5 | 1.5/0.75 | 3 μg/mm$^2$ | 80 MPa | ○ |
| Example 37 | 3G | 100 | 1 | SLS | 1.5 | POEL4 | 1.5 | 1.5/0.75 | 29 μg/mm$^2$ | 82 MPa | ○ |
| Example 38 | 3G | 100 | 5 | SLS | 1.5 | POEL4 | 1.5 | 1.5/0.75 | 2 μg/mm$^2$ | 76 MPa | ○ |

*3G has a water absorbing capacity of 1.7% by weight.

Example 39

A polymerizable monomer, water, a surfactant, a water-soluble polymer and a polymerization initiator were mixed together according to a composition shown in FIG. 10 to prepare a curable composition. The curable composition was measured for its amount of the unpolymerized product on the surfaces thereof. The results were as shown in Table 10.

Examples 40 to 43

Curable compositions were prepared in the same manner as in Example 39 but changing the kinds of the surfactant, and were measured for their amounts of the polymerized product on the surfaces thereof. The results were as shown in Table 10.

It will be learned from the results of Table 10 that use of the water-soluble polymer and the surfactant in combination makes it possible to greatly decrease the amount of the unpolymerized product formed on the surfaces.

TABLE 10

| | Polymerizable monomer | | Water | Water-soluble polymer | | Surfactant | | Polymerization | |
|---|---|---|---|---|---|---|---|---|---|
| | Kind | Blending amount (mass pts) | Blending amount (mass pts) | Kind | Blending amount (mass pts) | Kind | Blending amount (mass pts) | initiator BPO/DMPT (mass pts) | Unpolimerized product on surface |
| Comparative Example 21 | 3G | 100 | 3 | PVA1000 | 0.01 | — | — | 1.5/0.75 | 83 μg/mm$^2$ |
| Example 39 | 3G | 100 | 3 | PVA1000 | 0.01 | SLS | 1.5 | 1.5/0.75 | 3 μg/mm$^2$ |
| Example 40 | 3G | 100 | 3 | PVA1000 | 0.01 | SDS | 1.5 | 1.5/0.75 | 2 μg/mm$^2$ |
| Example 41 | 3G | 100 | 3 | PVA1000 | 0.01 | LDAGCl | 1.5 | 1.5/0.75 | 7 μg/mm$^2$ |
| Example 42 | 3G | 100 | 3 | PVA1000 | 0.01 | LTMACl | 1.5 | 1.5/0.75 | 18 μg/mm$^2$ |
| Example 43 | 3G | 100 | 3 | PVA1000 | 0.01 | POEL | 1.5 | 1.5/0.75 | 21 μg/mm$^2$ |

The invention claimed is:

1. A curable composition comprising:
    (A) 100 parts by mass of a monomer component which comprises a radically polymerizable monomer and has a water absorbing capacity of not larger than 20% by weight;
    (B) 0.5 to 5 parts by mass of water;
    (C) 0.1 to 20 parts by mass of a surfactant comprising an anionic surfactant (c-1) and a nonionic surfactant (c-2);
    (D) an effective amount of a radical polymerization initiator; and
    (E) a water-soluble polymer in an amount of 0.00001 to 10 parts by mass per 100 parts by mass of said monomer component (A),
wherein the curable composition is curable in the presence of the water.

2. A curable composition according to claim 1, wherein said monomer component (A) comprises a mixture of a strongly hydrophobic polymerizable monomer (a-1) having a water absorbing capacity of not larger than 5% by weight and a strongly hydrophilic polymerizable monomer (a-2) having a water absorbing capacity of not smaller than 100% by weight.

3. A curable composition according to claim 1, wherein said anionic surfactant (c-1) is contained in an amount of 0.1 to 10 parts by mass and said nonionic surfactant (c-2) is contained in an amount of 0.1 to 10 parts by mass per 100 parts by mass of said monomer component (A).

4. A curable composition according to claim 1, wherein said curable composition is cured by radical polymerization in a state of holding the water (B).

* * * * *